United States Patent
Pang et al.

(10) Patent No.: US 11,950,876 B2
(45) Date of Patent: Apr. 9, 2024

(54) UNGATED NON-CONTRAST ENHANCED MAGNETIC RESONANCE ANGIOGRAPHY USING MULTIPLE SUBSET RECONSTRUCTION AND TEMPORAL MAXIMUM INTENSITY PROJECTION

(71) Applicants: Siemens Healthineers AG, Forchheim (DE); NorthShore University HealthSystem, Evanston, IL (US)

(72) Inventors: Jianing Pang, Chicago, IL (US); Robert R. Edelman, Highland Park, IL (US); Ioannis Koktzoglou, Des Plaines, IL (US)

(73) Assignees: Siemens Healthineers AG, Forchheim (DE); NorthShore University HealthSystem, Evanston, IL (US)

( * ) Notice: Subject to any disclaimer, the term of this patent is extended or adjusted under 35 U.S.C. 154(b) by 171 days.

(21) Appl. No.: 16/994,778

(22) Filed: Aug. 17, 2020

(65) Prior Publication Data
US 2021/0045634 A1 Feb. 18, 2021

Related U.S. Application Data

(60) Provisional application No. 62/887,086, filed on Aug. 15, 2019.

(51) Int. Cl.
*A61B 5/00* (2006.01)
*A61B 5/055* (2006.01)
(Continued)

(52) U.S. Cl.
CPC .............. *A61B 5/004* (2013.01); *A61B 5/055* (2013.01); *A61B 5/7292* (2013.01);
(Continued)

(58) Field of Classification Search
CPC .............. G01R 33/563; G01R 33/5635; G01R 33/4838; G01R 33/4824; G01R 33/5608; A61B 5/055; A61B 5/7292; A61B 5/004
See application file for complete search history.

(56) References Cited

U.S. PATENT DOCUMENTS 6,505,064 B1 * 1/2003 Liu ...................... G06T 11/206
324/309
8,332,010 B2 12/2012 Edelman
(Continued)

OTHER PUBLICATIONS

Shin et al., "Characterization and suppression of stripe artifact in velocity-selective magnetization-prepared unenhanced MR angiography," (Mar. 13, 2018) Magn Reson Med, Nov. 2018, 80(5):1997-2005. (Year: 2018).*
(Continued)

*Primary Examiner* — Joel Lamprecht
*Assistant Examiner* — Ashish S Jasani

(57) ABSTRACT

A system and method for a non-contrast enhanced magnetic resonance imaging technique using a temporal maximum intensity projection reconstructed from multiple temporal subsets of data acquired the acquisition window. The method includes applying a radiofrequency pulse to the subject, waiting a quiescent interval, performing a radial acquisition with a golden-angle view angle increment over a duration corresponding to a cardiac cycle of the subject to generate acquisition data, reconstructing a plurality of images across a plurality of temporal phases from the acquisition data and generating a temporal maximum intensity projection image by tracking an intensity of each pixel across the plurality of images and selecting the pixel having a maximum intensity value across the plurality of images.

15 Claims, 4 Drawing Sheets

(51) Int. Cl.
*G01R 33/483* (2006.01)
*G01R 33/56* (2006.01)
*G01R 33/563* (2006.01)

(52) U.S. Cl.
CPC ..... *G01R 33/4838* (2013.01); *G01R 33/5608* (2013.01); *G01R 33/5635* (2013.01)

(56) References Cited

U.S. PATENT DOCUMENTS

| | | | |
|---|---|---|---|
| 9,113,810 B2 | 8/2015 | Edelman et al. | |
| 9,507,003 B2 | 11/2016 | Edelman et al. | |
| 2012/0243763 A1* | 9/2012 | Wen | G06T 5/50 382/131 |
| 2014/0018666 A1* | 1/2014 | Koktzoglou | A61B 5/055 600/419 |
| 2014/0126685 A1* | 5/2014 | Deuerling-Zheng | A61B 6/504 378/4 |

OTHER PUBLICATIONS

Koktzoglou et al., "Ungated Nonenhanced Radial Quiescent Interval Slice-Selective (QISS) Magnetic Resonance Angiography of the Neck: Evaluation of Image Quality," (May 11, 2019) J Magn Reson Imaging. Dec. 2019; 50(6): 1798-1807. (Year: 2019).*

Edelman et al., "Advances in non-contrast quiescent-interval slice-selective (QISS) magnetic resonance angiography," (Jan. 11, 2018) Clinical Radiology, 74:(1), pp. 29-36. (Year: 2018).*

Murayama et al. ,"Preliminary study of time maximum intensity projection computed tomography imaging for the detection of early ischemic change in patient with acute ischemic stroke," (Jan. 25, 2018), Medicine (2018) 97:9(e9906). (Year: 2018).*

Anderson et al. ,"Artifacts in Maximum-Intensity-Projection Display of MR Angiograms," (Aug. 1989), AJR 154:623-629, Mar. 1990 0361. (Year: 1989).*

Edelman, Robert R., et al. "Quiescent-interval single-shot unenhanced magnetic resonance angiography of peripheral vascular disease: technical considerations and clinical feasibility." Magnetic Resonance in Medicine: An Official Journal of the International Society for Magnetic Resonance in Medicine 63.4 (2010): 951-958.

Edelman, Robert R., et al. "Ungated radial quiescent-inflow single-shot (UnQISS) magnetic resonance angiography using optimized azimuthal equidistant projections." Magnetic resonance in medicine 72.6 (2014): 1522-1529.

Yokoyama, Kenichi, et al. "Non-contrast enhanced MR venography using 3D fresh blood imaging (FBI): initial experience." Radiation Medicine 19.5 (2001): 247-253. (abstract only).

* cited by examiner

UNGATED NON-CONTRAST ENHANCED MAGNETIC RESONANCE ANGIOGRAPHY USING MULTIPLE SUBSET RECONSTRUCTION AND TEMPORAL MAXIMUM INTENSITY PROJECTION

PRIORITY

The present application claims priority under 35 U.S.C. § 119(e) to U.S. provisional patent application No. 62/887,086, titled Ungated Non-Contrast Enhanced Magnetic Resonance Angiography Using Multiple Subset Reconstruction and Temporal Maximum Intensity Projection, filed Aug. 15, 2019, the disclosure of which is hereby incorporated by reference herein in its entirety.

TECHNICAL FIELD

The present disclosure is generally directed to magnetic resonance imaging. In one particular implementation, the present disclosure is directed to non-contrast enhanced magnetic resonance angiography (MRA).

BACKGROUND

MRA consists of a set of MRI-based techniques to image blood vessels. Some MRA techniques can include the use of a contrast agent to assist in the imaging of the blood vessels. However, the use of contrast agents may be undesirable and not suited for all patients. Accordingly, non-contrast MRA techniques have been developed. ECG gating is generally required for non-contrast MRA techniques for evaluating the lower extremity peripheral arteries, such as quiescent interval slice selective (QISS) and fresh blood imaging. ECG gating is a technique wherein magnetic resonance data acquisition is synchronized to the cardiac or respirator cycles of the subject in order to reduce cardiorespiratory artifacts on the resulting image. However, the use of ECG gating increases patient preparation time and may degrade image quality due to inaccurate triggering from arrhythmias or interference from the magnetohydrodynamic effect.

It has been previously demonstrated that the QISS technique may be modified to remove the ECG gating requirement and the image quality can often match that of ECG gated QISS. However, without ECG gating, the blood flow patterns during the application of in-plane and traveling venous suppression, as well as within the data acquisition window, are unpredictable and vary from slice to slice. Should a venous saturation pulse, placed inferior to the imaging slice, occur during a period of reverse flow, saturated arterial spins may inadvertently flow retrograde into the slice. A similar problem occurs when an in-plane saturation pulse is applied during a period of diastolic stasis when there is little or no inflow refreshment. In both situations, undesirable signal voids will occur in arteries. In a reformatted coronal view, such artifacts will show up as horizontal dark stripes across one or more arteries. For all of these reasons, non-contrast, non-ECG gated MRA or MRI-based techniques would be highly desirable in the art, especially in applications related to the imaging of a subject's peripheral arteries.

SUMMARY

In one general aspect, the present disclosure is directed to a method for imaging a subject, the method comprising: applying a radiofrequency pulse to the subject; after a quiescent interval, performing a radial acquisition over a duration corresponding to a cardiac cycle of the subject to generate acquisition data; reconstructing a plurality of images across a plurality of temporal phases from the acquisition data; and generating a temporal maximum intensity projection image by tracking an intensity of each pixel across the plurality of images and selecting the pixel having a maximum intensity value across the plurality of images.

In another general aspect, the present disclosure is directed to a medical imaging system comprising: an MRI machine; and a computer system coupled to the MRI machine, the computer system comprising: a processor; and a memory coupled to the processor, the memory storing instructions that, when executed by the processor, cause the computer system to: cause the MRI machine to apply a radiofrequency pulse to the subject; after a quiescent interval, cause the MRI machine to perform a radial acquisition over a duration corresponding to a cardiac cycle of the subject to generate acquisition data; reconstruct a plurality of images across a plurality of temporal phases from the acquisition data; and generate a temporal maximum intensity projection image by tracking an intensity of each pixel across the plurality of images and selecting the pixel having a maximum intensity value across the plurality of images.

FIGURES

The accompanying drawings, which are incorporated in and form a part of the specification, illustrate the embodiments of the invention and together with the written description serve to explain the principles, characteristics, and features of the invention. In the drawings.

DESCRIPTION

This disclosure is not limited to the particular systems, devices and methods described, as these may vary. The terminology used in the description is for the purpose of describing the particular versions or embodiments only, and is not intended to limit the scope.

As used in this document, the singular forms "a," "an," and "the" include plural references unless the context clearly dictates otherwise. Unless defined otherwise, all technical and scientific terms used herein have the same meanings as commonly understood by one of ordinary skill in the art.

Nothing in this disclosure is to be construed as an admission that the embodiments described in this disclosure are not entitled to antedate such disclosure by virtue of prior invention. As used in this document, the term "comprising" means "including, but not limited to."

Figure 1:
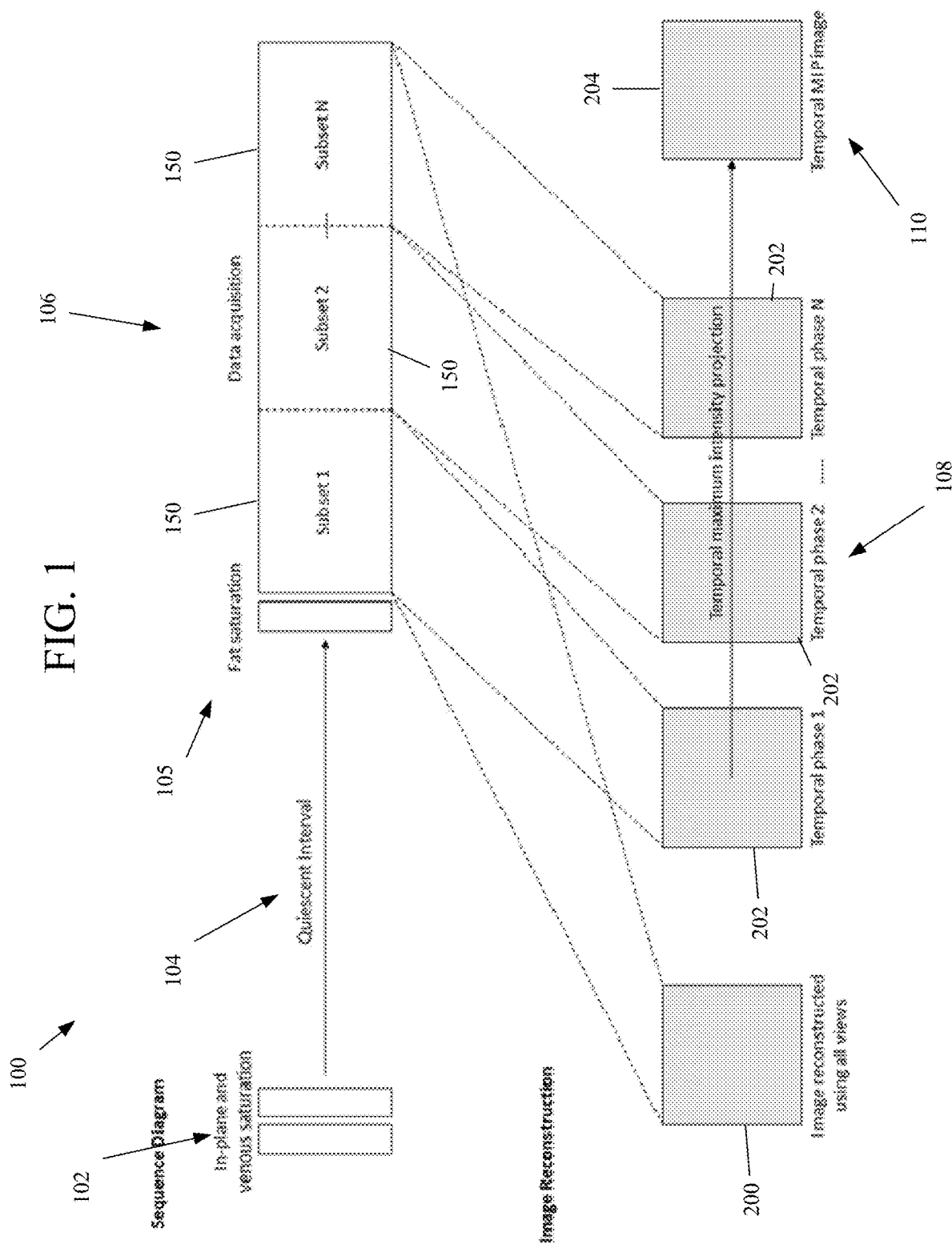
FIG. 1 depicts a sequence diagram of a process for obtaining an image of a subject reconstructed from a temporal maximum intensity projection from multiple temporal subsets in accordance with some embodiments.
Figure 2:
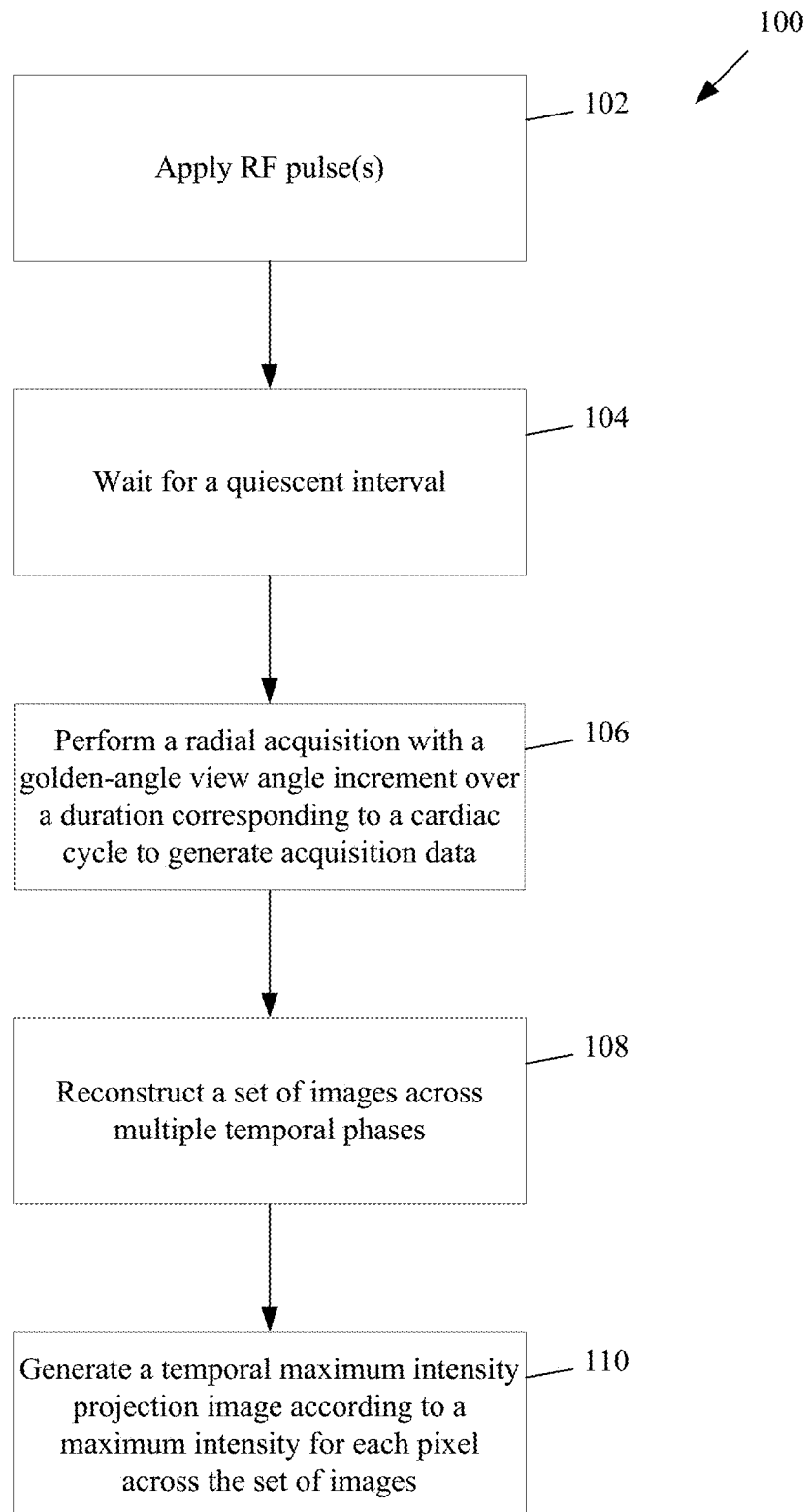
FIG. 2 depicts a flow diagram of the process depicted in FIG. 1 in accordance with some embodiments.

Referring now to FIGS. 1 and 2, there are shown various diagrams of a process 100 for obtaining an image of a subject reconstructed from a temporal maximum intensity projection (tMIP) from multiple temporal subsets. The process 100 can be executed by a computer system, such as the computer system 800 shown in FIG. 4 and described in greater detail below. Further, the process 100 can be embodied as software, hardware, firmware, or combinations thereof. In one embodiment, the process 100 can be embodied as instructions stored in a memory (e.g., a main memory 804 or a secondary memory 808) that, when executed by a processor (e.g., a processor 802) coupled to the memory, cause the computer system 800 to perform one or more steps of the process 100. Further, the computer system 800 can be operatively coupled to a MRI machine 900 such that the computer system 800 is able and configured to control operations of the MRI machine 900, cause the MRI machine 900 to image a subject positioned therein as is known in the medical imaging field, and receive data or signals from the MRI machine 900. In various embodiments, the computer system 800 can be integral to the MRI machine 900 or communicatively coupled to the MRI machine 900.

The presently described process 100 makes use of a technique referred to as quiescent interval slice selective (QISS) imaging. In QISS imaging, one or more initial RF pulses are applied to the subject and then the imaging system waits for a quiescent interval to allow for the inflow of arterial blood. In some embodiments, a fat suppression pulse can also be used to eliminate the fat signal. This is followed by data acquisition for image reconstruction. The goal of QISS imaging is to ensure high signal-to-noise ratio of arterial blood. In one embodiment, the QISS process can be repeated once every heartbeat, generating a stack of thin (e.g., 3 mm) slices that are combined together using a mean intensity projection (MIP). However, the process 100 described herein differs in that the image of the subject is reconstructed from a MIP across sequential subsets (temporal phases) of the acquisition data, which is referred to as a tMIP, rather than from a series of image slices of the subject (i.e., a spatial MIP).

Accordingly, the computer system 800 executing the process 100 can cause the MRI machine 900 to apply 102 one or more RF pulses to a subject positioned within the MRI machine 900, as is known in the medical imaging field. The computer system 800 can cause the MRI machine 900 to apply various different types of RF pulses. In one embodiment, the computer system 800 can cause the MRI machine 900 to apply an in-plane, traveling venous saturation pulse to the subject. In another embodiment, the computer system 800 can cause the MRI machine 900 to apply 105 a fat-suppression pulse to the subject in order to eliminate the fat signal generated during the quiescent interval.

Accordingly, the computer system 800 can wait 104 or pause for a quiescent interval. The quiescent interval can be any desired length of time. In one illustrative embodiment, the quiescent interval can be about 230 ms.

Accordingly, the computer system 800 can cause the MRI machine 900 to perform 106 a radial acquisition with a golden-angle view increment to generate acquisition data, which can then be used to reconstruct images of the subject therefrom. In one embodiment, the radial acquisition can be over a duration corresponding to a cardiac cycle. In one further embodiment, the duration can be equal to the average or expected cardiac cycle for the subject. A radial acquisition with a golden-angle view increment consists of continuously updating the view angle by a particular degree (approximately 111.25°) during the data acquisition window. Performing a radial acquisition with a golden-angle view increment is beneficial because the data generated at each view angle carries equal amounts of information, the view angles never repeat each other, and each view angle always adds complementary information to the previously acquired MRI data. Therefore, this technique is well-suited for continuous sampling. Further, using this technique allows for any arbitrary temporal subset of the sampled acquisition data to be used to generate an image of the subject, thereby allowing a user or the computer system 800 to balance temporal dynamics associated with the image reconstruction.

The acquired data can be divided into N data subsets 150 corresponding to N sequential temporal phases during the data acquisition window. As noted above, performing 106 a radial acquisition with a golden-angle view increment ensures that any arbitrary temporal subset of the sampled acquisition data can be used to generate an image of the subject. Accordingly, the computer system 800 can reconstruct 108 a set of N images 202 of the subject from the N sequential temporal subsets of the acquisition data. Using the images 202, the computer system 800 can then generate 110 a tMIP image 204 by tracking a maximum intensity for each pixel across the set of images 202. In other words, the computer system 800 can generate 110 the tMIP image 204 by, for each pixel in the images 202, determining the intensity value for each of the different versions of the pixel across the images 150, determining which version of the pixel across the images 150 had the highest intensity value, and then using the version of the pixel with the highest intensity value to reconstruct the tMIP image 204.

The process 100 described herein can be contrasted to conventional MRI techniques. In conventional MRI, a default image 200 is reconstructed from all of the acquired data, i.e., across the entire data acquisition window, as shown in FIG. 1. Conversely, in the process 100 described herein, the computer system 800 reconstructs 108 a set of N images 202 from N temporal subsets 150 of the acquired data and then reconstructs or generates 110 a composite image (i.e., the tMIP image 204) from the temporally subdivided images 202. The process 100 can provide numerous benefits, including eliminating vascular stripe artifacts associated with pulsatile flow and, in some applications, removing the need for ECG gating in non-contrast enhanced MRA of the lower extremity peripheral arteries.

Figure 3:
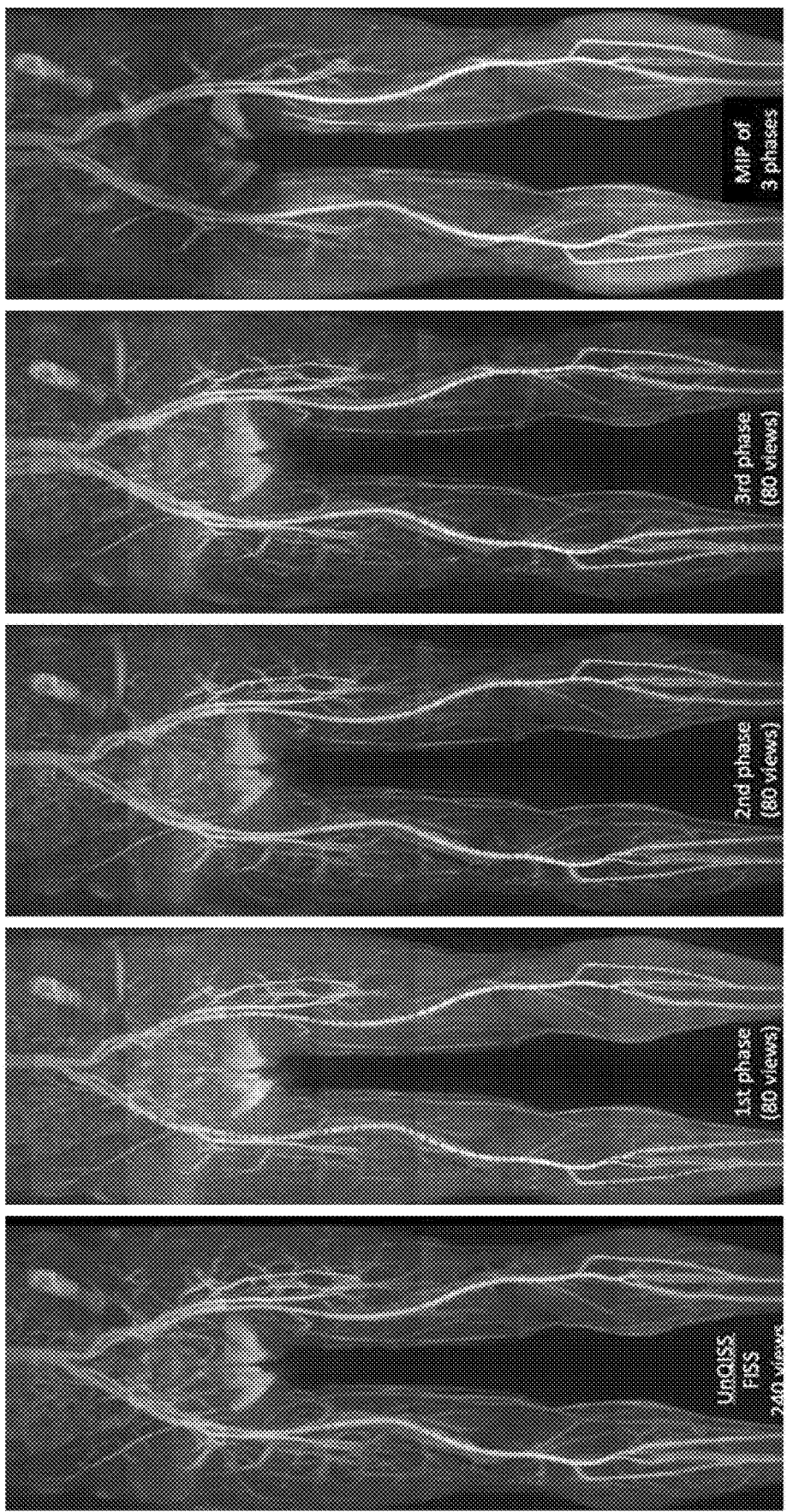
FIG. 3A depicts an image reconstructed using conventional magnetic resonance imaging techniques.
FIG. 3B depicts an image reconstructed from a first temporal subset generated by the process illustrated in FIG. 1 and FIG. 2 in accordance with some embodiments.
FIG. 3C depicts an image reconstructed from a second temporal subset generated by the process illustrated in FIG. 1 and FIG. 2 in accordance with some embodiments.
FIG. 3D depicts an image reconstructed from a third temporal subset generated by the process illustrated in FIG. 1 and FIG. 2 in accordance with some embodiments.
FIG. 3E depicts a temporal maximum intensity projection generated from the images shown in FIGS. 3B-3D in accordance with some embodiments.

FIGS. 3A-3E depict one illustrative application of the process 100. In this particular embodiment, a total of 240 radial views were acquired after the quiescent interval. The default image 200 reconstructed with all 240 views is shown in FIG. 3A. In this particular embodiment, the radial views were divided into three subsets 150 corresponding to three temporal phases (i.e., N=3). Further, three images 202 were reconstructed using views 1-80 (FIG. 3B), 81-160 (FIG. 3C), and 161-240 (FIG. 3D). Finally, a tMIP image 204 was then reconstructed from the three images 202, which is shown in FIG. 3E. The default image 200 demonstrated considerable dark stripe artifacts, which are also present to varying degrees and, importantly, at different spatial locations in the different temporal phase images 202. However, generating the tMIP image 204 from the three phase images 202 removes these artifacts and results in an overall improved imaging of the subject.

Although in this particular example 80 radial views were used to create each temporal phase image, this was simply for illustrative purposes and more or fewer radial views may be used. Further, although in this example three temporal phases were used, this was once again simply for illustrative purposes and more or fewer temporal phases could be used to reconstruct the tMIP image 204. In one embodiment, the acquisition window can span the duration of a typical cardiac cycle, so that at least one phase will likely coincide with brisk forward blood flow and, thus, provide a high arterial signal. If one phase has a high arterial signal, the tMIP reconstruction will suppress stripe artifacts that are present in images reconstructed from the full data set acquired across the entire acquisition window. It should also be noted that while the use of a golden angle radial acquisition is described herein, in other embodiments, other acquisition schemes can be used to generate the multiple subset images, such as radial imaging with alternative angular increments schemes or Cartesian imaging.

In one embodiment, the process 100 can be used in MRA. In other embodiments, the process 100 can be used in connection with other MRI-based applications or techniques.

Figure 4:
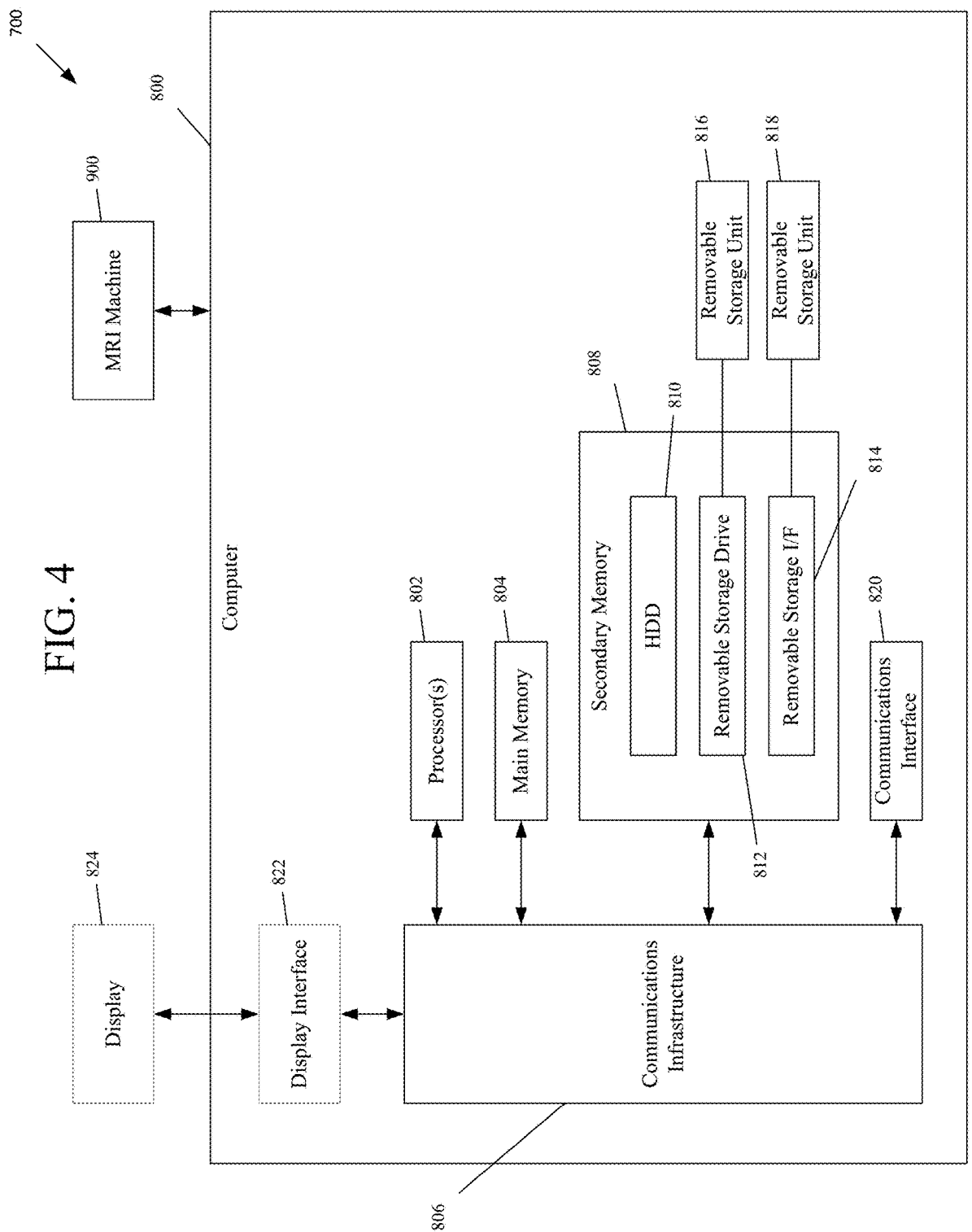
FIG. 4 depicts an architecture diagram of a medical imaging system that may be used in some embodiments.

FIG. 4 is an architecture diagram of a medical imaging system 700 that may be used in some embodiments. The medical imaging system 700 can include a computer system 800 and a MRI machine 900. The computer system 800 may include one or more processors 802. Each processor 802 is connected to a communication infrastructure 806 (e.g., a communications bus, cross-over bar, or network). Computer system 800 may include a display interface 822 that forwards graphics, text, and other data from the communication infrastructure 806 (or from a frame buffer, not shown) for display on the display unit 824.

Computer system 800 may also include a main memory 804, such as a random access memory (RAM), and a secondary memory 808. The secondary memory 808 may include, for example, a hard disk drive (HDD) 810 and/or removable storage drive 812, which may represent a floppy disk drive, a magnetic tape drive, an optical disk drive, a memory stick, or the like as is known in the art. The removable storage drive 812 reads from and/or writes to a removable storage unit 816. Removable storage unit 816 may be a floppy disk, magnetic tape, optical disk, or the like. As will be understood, the removable storage unit 816 may include a computer readable storage medium having tangibly stored therein (embodied thereon) data and/or computer software instructions, e.g., for causing the processor(s) to perform various operations.

In alternative embodiments, secondary memory 808 may include other similar devices for allowing computer programs or other instructions to be loaded into computer system 800. Secondary memory 808 may include a removable storage unit 818 and a corresponding removable storage interface 814, which may be similar to removable storage drive 812, with its own removable storage unit 816. Examples of such removable storage units include, but are not limited to, USB or flash drives, which allow software and data to be transferred from the removable storage unit 816, 818 to computer system 800.

Computer system 800 may also include a communications interface 820. Communications interface 820 allows software and data to be transferred between computer system 800 and external devices. Examples of communications interface 820 may include a modem, Ethernet card, wireless network card, a Personal Computer Memory Card International Association (PCMCIA) slot and card, or the like.

Software and data transferred via communications interface 820 may be in the form of signals, which may be electronic, electromagnetic, optical, or the like that are capable of being received by communications interface 820. These signals may be provided to communications interface 820 via a communications path (e.g., channel), which may be implemented using wire, cable, fiber optics, a telephone line, a cellular link, a radio frequency (RF) link and other communication channels.

In this document, the terms "computer program medium" and "non-transitory computer-readable storage medium" refer to media such as, but not limited to, media at removable storage drive 812, or a hard disk installed in hard disk drive 810, or removable storage unit 816. These computer program products provide software to computer system 800. Computer programs (also referred to as computer control logic) may be stored in main memory 804 and/or secondary memory 808. Computer programs may also be received via communications interface 820. Such computer programs, when executed by a processor, enable the computer system 800 to perform the features of the methods discussed herein. For example, main memory 804, secondary memory 808, or removable storage units 816 or 818 may be encoded with computer program code (instructions) for performing operations corresponding to various processes disclosed herein.

It is understood by those familiar with the art that the system described herein may be implemented in hardware, firmware, or software encoded (e.g., as instructions executable by a processor) on a non-transitory computer-readable storage medium.

While various illustrative embodiments incorporating the principles of the present teachings have been disclosed, the present teachings are not limited to the disclosed embodiments. Instead, this application is intended to cover any variations, uses, or adaptations of the present teachings and use its general principles. Further, this application is intended to cover such departures from the present disclosure that are within known or customary practice in the art to which these teachings pertain.

In the above detailed description, reference is made to the accompanying drawings, which form a part hereof. In the drawings, similar symbols typically identify similar components, unless context dictates otherwise. The illustrative embodiments described in the present disclosure are not meant to be limiting. Other embodiments may be used, and other changes may be made, without departing from the spirit or scope of the subject matter presented herein. It will be readily understood that various features of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various features. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein are generally intended as "open" terms (for example, the term "including" should be interpreted as "including but not limited to," the term "having" should be interpreted as "having at least," the term "includes" should be interpreted as "includes but is not limited to," et cetera). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

In addition, even if a specific number is explicitly recited, those skilled in the art will recognize that such recitation should be interpreted to mean at least the recited number (for example, the bare recitation of "two recitations," without other modifiers, means at least two recitations, or two or more recitations). Furthermore, in those instances where a convention analogous to "at least one of A, B, and C, et cetera" is used, in general such a construction is intended in the sense one having skill in the art would understand the convention (for example, "a system having at least one of A, B, and C" would include but not be limited to systems that have A alone, B alone, C alone, A and B together, A and C together, B and C together, and/or A, B, and C together, et cetera). In those instances where a convention analogous to "at least one of A, B, or C, et cetera" is used, in general such a construction is intended in the sense one having skill in the art would understand the convention (for example, "a system having at least one of A, B, or C" would include but not be limited to systems that have A alone, B alone, C alone, A and B together, A and C together, B and C together, and/or A, B, and C together, et cetera). It will be further understood by those within the art that virtually any disjunctive word and/or phrase presenting two or more alternative terms, whether in the description, sample embodiments, or drawings, should be understood to contemplate the possibilities of including one of the terms, either of the terms, or both terms. For example, the phrase "A or B" will be understood to include the possibilities of "A" or "B" or "A and B."

In addition, where features of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, et cetera. As a non-limiting example, each range discussed herein can be readily broken down into a lower third, middle third and upper third, et cetera. As will also be understood by one skilled in the art all language such as "up to," "at least," and the like include the number recited and refer to ranges that can be subsequently broken down into subranges as discussed above. Finally, as will be understood by one skilled in the art, a range includes each individual member.

Thus, for example, a group having 1-3 components refers to groups having 1, 2, or 3 components. Similarly, a group having 1-5 components refers to groups having 1, 2, 3, 4, or 5 components, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. A method for imaging a subject, the method comprising:
   applying a radiofrequency pulse to the subject;
   after a quiescent interval, performing a radial acquisition over a duration corresponding to a cardiac cycle of the subject to generate acquisition data;
   reconstructing a plurality of 2-D images across a plurality of sequential temporal phases within the duration from the acquisition data, each of the 2-D images depicting a same partial cross-section of the subject and being reconstructed from a continuously sampled subset of the plurality of the sequential temporal phases; and
   generating a temporal maximum intensity projection image of the same partial cross-section of the subject by tracking an intensity of each pixel across the plurality of 2-D images and selecting a maximum intensity value for the pixel across the plurality of 2-D images, which corresponds to a maximum intensity during the cardiac cycle, such that vascular stripe artifacts in the temporal maximum intensity projection image are removed relative to the plurality of 2-D images.

2. The method of claim 1, wherein applying the radiofrequency pulse to the subject comprises applying in-plane and traveling venous saturation pulses to the subject.

3. The method of claim 1, wherein applying the radiofrequency pulse to the subject comprises applying a fat-suppression pulse to the subject.

4. The method of claim 1, wherein the radial acquisition is configured to image peripheral blood vessels of the subject.

5. The method of claim 1, wherein the cardiac cycle comprises an average cardiac cycle of the subject.

6. The method of claim 1, wherein the performing the radial acquisition comprises a golden-angle view angle increment.

7. A medical imaging system comprising:
   an MRI machine; and
   a computer system coupled to the MRI machine, the computer system comprising:
      a processor; and
      a memory coupled to the processor, the memory storing instructions that, when executed by the processor, cause the computer system to:
         cause the MRI machine to apply a radiofrequency pulse to a subject;
         after a quiescent interval, cause the MRI machine to perform a radial acquisition over a duration corresponding to a cardiac cycle of the subject to generate acquisition data;
         reconstruct a plurality of 2-D images across a plurality of sequential temporal phases within the duration from the acquisition data, each of the 2-D images depicting a same partial cross-section of— the subject and being reconstructed from a continuously sampled subset of the plurality of the sequential temporal phases; and generate a temporal maximum intensity projection image of the same partial cross-section of the subject by tracking an intensity of each pixel across the plurality of 2-D images and selecting a maximum intensity value for the pixel across the plurality of 2-D images, which corresponds to a maximum intensity during the cardiac cycle, such that vascular stripe artifacts in the temporal maximum intensity projection image are removed relative to the plurality of 2-D images.

8. The medical imaging system of claim 7, wherein the memory stores instructions that, when executed by the processor, cause the MRI machine to apply the radiofrequency pulse to the subject by applying in-plane and traveling venous saturation pulses to the subject.

9. The medical imaging system of claim 7, wherein the memory stores instructions that, when executed by the processor, cause the MRI machine to apply the radiofrequency pulse to the subject by applying a fat-suppression pulse to the subject.

10. The medical imaging system of claim 7, wherein the radial acquisition is configured to image peripheral blood vessels of the subject.

11. The medical imaging system of claim 7, wherein the cardiac cycle comprises an average cardiac cycle of the subject.

12. The medical imaging system of claim 7, wherein the radial acquisition comprises a golden-angle view angle increment.

13. The method of claim 1, further comprising dividing the acquisition data into a plurality of sequential subsets.

14. The method of claim 13, wherein the plurality of sequential temporal phases correspond to the plurality of sequential subsets.

15. The method of claim 1, wherein the continuously sampled subset is sampled over a view increment.

* * * * *